US012766808B2

(12) United States Patent
Takada et al.

(10) Patent No.: US 12,766,808 B2
(45) Date of Patent: Oct. 20, 2026

(54) COMPOSITE ABSORBENT BODY AND POLYMERIC ABSORBER

(71) Applicant: ORGANO CORPORATION, Tokyo (JP)

(72) Inventors: Hitoshi Takada, Tokyo (JP); Ryouta Iwaura, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 661 days.

(21) Appl. No.: 18/270,030

(22) PCT Filed: Dec. 15, 2021

(86) PCT No.: PCT/JP2021/046314
§ 371 (c)(1),
(2) Date: Jun. 28, 2023

(87) PCT Pub. No.: WO2022/145237
PCT Pub. Date: Jul. 7, 2022

(65) Prior Publication Data

US 2024/0116263 A1 Apr. 11, 2024

(30) Foreign Application Priority Data

Dec. 29, 2020 (JP) ................................ 2020-219829

(51) Int. Cl.
*B32B 5/18* (2006.01)
*A61F 13/53* (2006.01)
(Continued)

(52) U.S. Cl.
CPC ................ *B32B 5/18* (2013.01); *A61F 13/53* (2013.01); *B32B 3/04* (2013.01); *B32B 5/02* (2013.01);
(Continued)

(58) Field of Classification Search
None
See application file for complete search history.

(56) References Cited

U.S. PATENT DOCUMENTS 5,900,146 A 5/1999 Ballard et al.
7,179,951 B2 * 2/2007 Krishnaswamy-Mirle ................. B32B 5/26 604/378

(Continued)

FOREIGN PATENT DOCUMENTS

JP 10-505118 A 5/1998
JP 3231320 B2 9/2001

(Continued)

OTHER PUBLICATIONS

International Search Report issued Mar. 1, 2022, in International Bureau of Wipo Patent Application No. PCT/JP2021/046314, with an English translation thereof.

(Continued)

*Primary Examiner* — John J Figueroa
(74) *Attorney, Agent, or Firm* — Greenblum & Bernstein, P.L.C.

(57) ABSTRACT

A composite absorbent body for absorbing a liquid and for use as a sanitary article contains a polymeric absorber equipped with a hydrophilic continuous framework and continuous pores. The ratio of pore volume from pores having a pore radius of 1 μm or higher in the polymeric absorber is at least 90% of the pore volume of all pores.

12 Claims, 9 Drawing Sheets

(51) Int. Cl.

| | |
|---|---|
| ***B32B 3/04*** | (2006.01) |
| ***B32B 5/02*** | (2006.01) |
| ***B32B 5/24*** | (2006.01) |

(52) U.S. Cl.

CPC ...... *B32B 5/245* (2013.01); *B32B 2266/0214* (2013.01); *B32B 2266/104* (2016.11); *B32B 2307/726* (2013.01); *B32B 2307/728* (2013.01)

(56) References Cited

U.S. PATENT DOCUMENTS

| | | | | |
|---|---|---|---|---|
| 8,921,244 | B2 * | 12/2014 | Cabell | D06M 23/08<br>442/350 |
| 9,238,089 | B2 * | 1/2016 | Chmielewski | A61F 13/531 |
| 2005/0130542 | A1 * | 6/2005 | Klein | D04H 1/593<br>442/403 |
| 2018/0000663 | A1 * | 1/2018 | Nishida | A61L 15/425 |
| 2019/0119452 | A1 | 4/2019 | Yoon et al. | |
| 2019/0275781 | A1 * | 9/2019 | Riehle | B32B 37/12 |
| 2019/0343978 | A1 * | 11/2019 | McEneany | C08J 9/0061 |
| 2022/0331776 | A1 | 10/2022 | Takada et al. | |

FOREIGN PATENT DOCUMENTS

| | | | |
|---|---|---|---|
| JP | 2003-102784 | A | 4/2003 |
| JP | 2009-221428 | A | 10/2009 |
| JP | 2017-137432 | A | 8/2017 |
| WO | 93/04092 | A1 | 3/1993 |
| WO | 96/07675 | A1 | 3/1996 |
| WO | 2020/261929 | A1 | 12/2020 |
| WO | 2020/262343 | A1 | 12/2020 |
| WO | 2021/131301 | A1 | 7/2021 |

OTHER PUBLICATIONS

Written Opinion issued Mar. 1, 2022, in International Bureau of WIPO Patent Application No. PCT/JP2021/046314, with an English translation thereof.

* cited by examiner (ABSORBENT A)

COMPOSITE ABSORBENT BODY AND POLYMERIC ABSORBER

FIELD

The present invention relates to a composite absorbent body and to a polymer absorbent.

BACKGROUND

Absorbent bodies comprising porous materials such as sponge materials are known for absorption of liquids such as aqueous solutions. PTL 1, for example, discloses an absorbent article comprising a polymer foam material made of a hydrophilic flexible structure with interconnected open cells.

CITATION LIST

Patent Literature

[PTL 1] Japanese Patent Publication No. 3231320

SUMMARY

Technical Problem

Research by the present inventors has shown that porous materials such as the polymer foam material of PTL 1 contain numerous pores with relatively small pore radii. In a porous structure, however, liquid components tend to be drawn more easily into pores with relatively large pore radii. Consequently, liquid components may fail to infiltrate into the pores of small pore size when absorbed by such porous materials that have more pores of smaller pore size, and this can potentially result in lower liquid absorption for their pore volume.

The present invention has been devised in light of the aforementioned problems, and its object is to provide a composite absorbent body and polymer absorbent that can inhibit reduction in liquid absorption in proportion to pore volume, and that exhibits excellent absorption performance.

Solution to Problem

One aspect of the invention (aspect 1) is a composite absorbent body for absorption of liquid, comprising a polymer absorbent comprising a hydrophilic continuous skeleton and continuous pore, wherein a ratio of a pore volume of a pore with a pore radius of 1 μm or greater in the polymer absorbent is 90% or more of a pore volume of the pore.

In the composite absorbent body of this aspect, the ratio of the pore volume of the pore with a pore radius of 1 μm or greater in the polymer absorbent is at least 90% of the pore volume of the pore. Thus, while it is difficult for liquid to infiltrate into pores of relatively smaller pore radii, such as pore radii of less than 1 μm, nevertheless the liquid can be taken up into pores with pore radii of 1 μm or greater, allowing liquid absorption to be adequately ensured. Reduction in liquid absorption in proportion to pore volume can thus be inhibited, allowing excellent absorption performance to be obtained.

According to another aspect (aspect 2) of the invention, in the polymer absorbent of the composite absorbent body of aspect 1, the ratio of the pore volume of the pore with the pore radius of 0.005 μm or smaller is less than 10% of the pore volume of the pore.

The composite absorbent body of this aspect has a very low ratio for the pore volume of the pore with extremely small pore radius which is less able to absorb liquids, such as a pore radius of 0.005 μm or smaller, and has a large ratio for the pore volume of the pore of large pore radius which is able to absorb liquids, such as a pore radius of 1 μm or greater. This allows the pores of the polymer absorbent to be effectively used for liquid absorption, to ensure an adequate amount of liquid absorption.

According to yet another aspect (aspect 3) of the invention, in the polymer absorbent of the composite absorbent body of aspect 1 or 2, the pore radius at a maximum value of the pore volume is 500 μm or smaller.

The composite absorbent body of this aspect, having 500 μm or smaller as the pore radius at a maximum pore volume, can inhibit disintegration (collapse) of the continuous skeleton structure of the polymer absorbent during liquid absorption, to help provide an excellent absorption rate, and can stably ensure an adequate amount of liquid absorption (i.e. the continuous skeleton structure may not be supported and may collapse during liquid absorption if the pore radius at the maximum pore volume is greater than 500 μm).

According to yet another aspect (aspect 4) of the invention, in the polymer absorbent of the composite absorbent body according to any one of aspects 1 to 3, a coefficient of variation of a pore distribution in the pore with the pore radius of 1 μm or greater is 1.4 or smaller.

Since the coefficient of variation of the pore distribution in the composite absorbent body of this aspect is 1.4 or smaller, there is less variation in pore radius with respect to the average pore radius, resulting in a sharp peak representing the pore distribution near the average pore radius. The polymer absorbent can therefore absorb liquids approximately evenly in all directions over the entire surface. This allows the pores of the polymer absorbent to be effectively used for liquid absorption, to ensure an adequate amount of liquid absorption.

According to yet another aspect (aspect 5) of the invention, in the polymer absorbent in the composite absorbent body according to any one of aspects 1 to 3, a coefficient of variation of a pore distribution in the pore with the pore radius of 1 μm or greater is larger than 1.4.

Since the coefficient of variation of the pore distribution in the composite absorbent body of this aspect is larger than 1.4, there is high variation in pore radius with respect to the average pore radius, resulting in a broad peak representing the pore distribution near the average pore radius. In other words, the polymer absorbent has both pores with small pore radii and pores with large pore radii. Consequently, capillary action takes place more easily in the pores with small pore radii, resulting in a faster liquid absorption rate, while the liquid absorption volume tends to increase in the pores with large pore radii. As a result, a synergistic effect is exhibited by both, allowing the polymer absorbent to instantly absorb large amounts of liquid into the pores.

According to yet another aspect (aspect 6) of the invention, in the polymer absorbent of the composite absorbent body according to aspect 5, for the pore radius corresponding to a local maximum value of the pore volume in a pore distribution curve, a region on a side with a larger pore radius is broader than a region on a side with a smaller pore radius.

The polymer absorbent in the composite absorbent body of this aspect has the aforementioned structure, i.e., a structure with more pores of large pore size than pores with small pore radii. By having more pores with large pore radii, the liquid absorption volume tends to increase, allowing absorption of larger amounts of liquid into the pores.

According to yet another aspect (aspect 7) of the invention, in the polymer absorbent of the composite absorbent body according to aspect 5, for the pore radius corresponding to a local maximum value of the pore volume in a pore distribution curve, a region on a side with a smaller pore radius is broader than a region on a side with a larger pore radius.

The polymer absorbent in the composite absorbent body of this aspect has the aforementioned structure, i.e., a structure with more pores of small pore size than pores with large pore radii. By having more pores with small pore radii, the capillary action tends to take place more easily, thus further increasing the liquid absorption rate and allowing more instant absorption of liquid into the pores.

According to yet another aspect (aspect 8) of the invention, in the polymer absorbent of the composite absorbent body according to any one of aspects 1 to 3, there are at least two local maximum values of the pore volume in a pore distribution curve.

The polymer absorbent in the composite absorbent body of this aspect has the aforementioned structure, i.e., it has both pores with the prescribed small pore radii and pore radii in that vicinity, and pores with the prescribed larger pore radii and pore radii in that vicinity. Consequently, capillary action takes place more easily in the pores with relatively small pore radii, resulting in a faster liquid absorption rate, while the liquid absorption volume tends to be greater in the pores with relatively large pore radii. As a result, a synergistic effect is exhibited by both, allowing the polymer absorbent to instantly absorb large amounts of liquid into the pores.

According to yet another aspect (aspect 9) of the invention, in the polymer absorbent of the composite absorbent body according to aspect 8, of the two local maximum values of the pore volume in the pore distribution curve, a relatively small local maximum value of the pore radius is greater than a relatively large local maximum value of the pore radius.

The polymer absorbent in the composite absorbent body of this aspect has the aforementioned structure, i.e., a structure with more pores of small pore size than pores with large pore radii. By having more pores with small pore radii, capillary action tends to take place more easily, thus further increasing the liquid absorption rate and allowing more instant absorption of liquid into the pores.

According to yet another aspect (aspect 10) of the invention, for the polymer absorbent of the composite absorbent body according to aspect 8, of the two local maximum values of the pore volume in the pore distribution curve, a relatively small local maximum value of the pore radius is smaller than a relatively large local maximum value of the pore radius.

The polymer absorbent in the composite absorbent body of this aspect has the aforementioned structure, i.e., a structure with more pores of large pore size than pores with small pore radii. By having more pores with large pore radii, the liquid absorption volume tends to increase, allowing absorption of larger amounts of liquid into the pores.

According to yet another aspect (aspect 11) of the invention, in the polymer absorbent in the composite absorbent body according to any one of aspects 1 to 10, a total pore volume is 0.9 mL/g or greater.

Since the polymer absorbent in the composite absorbent body of this aspect has a total pore volume of 0.9 mL/g or greater, sufficient pore volume can be ensured for the polymer absorbent, thus making it possible to ensure an adequate amount of liquid absorption. During absorption, this can also help prevent collapse of the spaces (pores) for uptake of liquids to be absorbed by the porous body, and can help prevent reduction in the amount and speed of liquid absorption.

According to yet another aspect (aspect 12) of the invention, in the polymer absorbent in the composite absorbent body according to any one of aspects 1 to 11, a bulk density is 0.07 to 0.6 g/cm$^3$.

Since the bulk density of the polymer absorbent in the composite absorbent body of this aspect is 0.07 to 0.6 g/cm$^3$, liquid absorption rate (DW) performance of 6 mL/30 sec or greater can be exhibited. In other words, because the liquid absorption rate is faster the polymer absorbent can more instantly absorb liquid into the pores.

According to yet another aspect (aspect 13) of the invention, the polymer absorbent in the composite absorbent body according to any one of aspects 1 to 12 is a monolithic absorbent.

Since the polymer absorbent in the composite absorbent body of this aspect is a monolithic absorbent, it is able to rapidly absorb liquids.

According to yet another aspect (aspect 14) of the invention, the polymer absorbent in the composite absorbent body according to any one of aspects 1 to 13 is a crosslinked polymer hydrolysate of a compound comprising a (meth) acrylic acid ester and two or more vinyl groups in the molecule, and contains at least one or more —COONa group.

If the polymer absorbent in the composite absorbent body of this aspect has this specified construction, then the hydrophilic continuous skeleton will tend to extend and the continuous pore will tend to widen during absorption of liquids, thus allowing more liquid to be more rapidly taken up into the continuous pore and exhibiting even more excellent absorption performance as an absorbent body.

Yet another aspect of the invention (aspect 15) is a polymer absorbent comprising a hydrophilic continuous skeleton and continuous pore, wherein a ratio of a pore volume of a pore with a pore radius of 1 μm or greater is at least 90% of the pore volume of the pore.

Since the ratio of the pore volume of the pore with pore radius of 1 μm or greater in the polymer absorbent of this aspect is at least 90% of the pore volume of the pore, during liquid absorption it is possible to ensure an adequate amount of liquid absorption even without uptake of liquids into the pore with relatively small pore radius, such as a pore radius of less than 1 μm. This can inhibit reduction in liquid absorption in proportion to pore volume, allowing excellent absorption performance to be obtained.

Advantageous Effects of Invention

According to the invention it is possible to provide a composite absorbent body that can inhibit reduction in liquid absorption in proportion to pore volume, and that exhibits excellent absorption performance, as well as sanitary products comprising the same.

DESCRIPTION OF EMBODIMENTS

A preferred embodiment of the invention will now be described in detail using the composite absorbent body 1 as an embodiment.

Throughout the present specification, unless otherwise specified, the concept of "viewing an object (for example, a composite absorbent body) on the horizontal plane in the expanded state in the thickness direction of the object, from the upper side in the vertical direction", will be referred to by the phrase "as viewed plane".

[Composite Absorbent Body]

Figure 1:
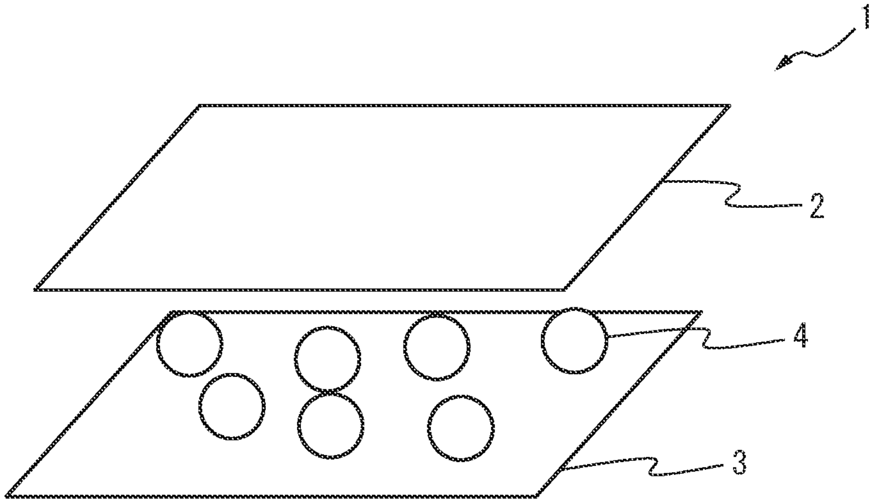
FIG. 1 is an exploded perspective view of a composite absorbent body 1 according to an embodiment of the invention.

FIG. 1 is an exploded perspective view of a composite absorbent body 1 according to one embodiment of the invention.

The composite absorbent body 1 shown in FIG. 1 comprises a first retaining sheet 2 having an approximately rectangular outer shape as viewed plane and forming the surface on one side of the composite absorbent body 1, in the thickness direction, a second retaining sheet 3 forming the surface on the other side of the composite absorbent body 1, and a liquid absorbing member situated between the two aforementioned sheets and comprising a polymer absorbent 4.

The liquid absorbing member in the composite absorbent body 1 is situated between the first retaining sheet 2 and second retaining sheet 3 and includes a polymer absorbent 4 having a hydrophilic continuous skeleton and continuous pores, allowing it to absorb and retain liquid that has permeated through the first retaining sheet 2.

The polymer absorbent 4 also exhibits characteristic liquid absorbing behavior, whereby during absorption of liquid, the liquid is taken up into the continuous pores after having been taken up into the continuous skeleton.

During absorption of a liquid such as an aqueous solution, the liquid is instantly taken up into the hydrophilic continuous skeleton of the polymer absorbent 4 by osmotic pressure, resulting in expansion, thereby increasing the volume of the continuous pores and allowing liquid to be taken up into the enlarged continuous pores, and thus allowing a larger amount of liquid to be instantly absorbed, the absorbed liquid also being delivered into the SAP which has high water retention capacity, and being firmly held in the SAP.

This allows the composite absorbent body 1 containing the polymer absorbent 4 to exhibit high absorption performance as an absorbent body.

According to the invention, the liquid absorbing member is not limited to the aspects of the composite absorbent body 1 of this embodiment, and the liquid absorbing member may also include other liquid-absorbing materials so long as it includes the polymer absorbent exhibiting at least the characteristic liquid absorbing behavior described above. For example, the liquid absorbing member disposed between the first retaining sheet 2 and second retaining sheet 3 may be made of a mixture of the polymer absorbent 4 and superabsorbent polymer 5 (SAP), as in the composite absorbent body 1' of another embodiment of the invention shown in FIG. 2.

Figure 2:
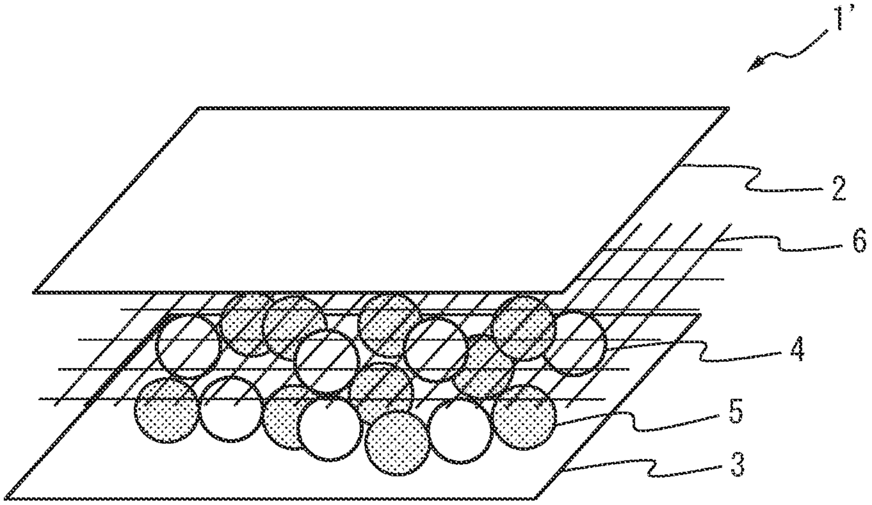
FIG. 2 is an exploded perspective view of a composite absorbent body 1' according to another embodiment of the invention.

The structure of the composite absorbent body of the invention is also not limited to the aspects of the composite absorbent body 1 of this embodiment, and for example, the composite absorbent body may also have a hydrophilic fiber sheet 6 situated between the first retaining sheet 2 and the liquid absorbing member (that is, the polymer absorbent 4 and superabsorbent polymer 5), as in the composite absorbent body 1' of the other embodiment of the invention shown in FIG. 2.

According to the invention, the outer shape and various dimensions and basis weight of the composite absorbent body are not particularly restricted so long as the effect of the invention is not inhibited, and any desired outer shape (such as circular, oblong, polygonal, hourglass or design shape), and dimensions and basis weight, may be employed depending on the intended purpose and manner of use.

Each of the structural members of the composite absorbent body of the invention will now be explained in further detail using the composite absorbent body 1 of the embodiment shown in FIG. 1 as an example.

(Retaining Sheet)

In the composite absorbent body 1 shown in FIG. 1, the first retaining sheet 2 forming the surface on one side of the composite absorbent body 1 has an approximately rectangular outer shape similar to the outer shape of the composite absorbent body 1, as viewed plane. The first retaining sheet 2 may be formed of a liquid-permeable sheet-like member that allows permeation of liquid supplied to the composite absorbent body 1 and causes it to be absorbed and retained in the inner liquid absorbing member.

The first retaining sheet 2 has a slightly larger size overall compared to the liquid absorbing member situated on the inner side (that is, compared to the regions where the liquid-absorbing materials such as the polymer absorbent 4 are situated), while at the perimeter edges it is bonded with the second retaining sheet 3 situated on the other side in the thickness direction of the composite absorbent body 1, using any adhesive or heat sealing means.

The second retaining sheet 3 forming the surface on the other side of the composite absorbent body 1 likewise has an approximately rectangular outer shape similar to the outer shape of the composite absorbent body 1, as viewed plane. The second retaining sheet 3 is formed of a liquid-impermeable sheet-like member that prevents liquid that was not absorbed and retained by the inner liquid absorbing member and liquid that has seeped from the liquid absorbing member, from leaking out of the composite absorbent body 1.

According to the invention, the respective sheet-like members to be used for the first retaining sheet and second retaining sheet are not limited to this embodiment, and the composite absorbent body of the invention may have the retaining sheets of either or both the first retaining sheet and second retaining sheet formed of liquid-permeable sheet-like members. In other words, the composite absorbent body of the invention may have the retaining sheet of either the first retaining sheet or second retaining sheet formed of a liquid-impermeable sheet-like member.

When a liquid-permeable sheet-like member is used as a retaining sheet, the liquid-permeable sheet-like member is not particularly restricted so long as it does not interfere with the effect of the invention, and any liquid-permeable sheet-like member may be employed, depending on the purpose and intended usage. Examples of liquid-permeable sheet-like members include nonwoven fabrics such as hydrophilic air-through nonwoven fabrics, spunbonded nonwoven fabrics and point-bonded nonwoven fabrics, or woven fabrics, knitted fabrics and porous resin films.

When a hydrophilic nonwoven fabric, woven fabric or knitted fabric (hereunder collectively referred to as "fiber sheet") is used as the liquid-permeable sheet-like member, the fiber sheet may have a monolayer structure or a multilayer structure with two or more layers. The type of constituent fibers of the fiber sheet is not particularly restricted, and examples include hydrophilic fibers such as cellulosic fibers or hydrophilic-treated thermoplastic resin fibers. Such fibers may be used alone, or two or more different types of fibers may be used in combination.

Examples of cellulosic fibers to be used as constituent fibers for the fiber sheet include natural cellulose fibers (such as cotton or other plant fibers), regenerated cellulose fibers, refined cellulose fibers and semi-synthetic cellulose fibers. Examples of thermoplastic resin fibers to be used as constituent fibers for the fiber sheet include fibers made of publicly known thermoplastic resins, including olefin-based resins such as polyethylene (PE) and polypropylene (PP), polyester-based resins such as polyethylene terephthalate (PET), and polyamide-based resins such as 6-nylon. Such resins may be used alone, or two or more resins may be used in combination.

When a liquid-impermeable sheet-like member is used as a retaining sheet, the liquid-impermeable sheet-like member is not particularly restricted so long as it does not interfere with the effect of the invention, and any liquid-impermeable sheet-like member may be employed, depending on the purpose and intended usage. Examples of such liquid-impermeable sheet-like members include hydrophobic nonwoven fabrics formed of any desired hydrophobic thermoplastic resin fibers (for example, polyolefin-based fibers such as PE and PP, polyester-based fibers such as PET, and various composite fibers such as core-sheath fibers); porous or non-porous resin films formed of hydrophobic thermoplastic resins such as PE or PP; laminates of nonwoven fabrics attached to resin films; and layered nonwoven fabrics such as SMS nonwoven fabrics.

According to the invention, the outer shape and various dimensions and basis weight of the retaining sheet are not particularly restricted so long as the effect of the invention is not inhibited, and any desired outer shape (such as circular, oblong, polygonal, hourglass or design shape), and dimensions and basis weight, may be employed depending on the intended purpose and manner of use.

(Liquid Absorbing Member)

The liquid absorbing member in the composite absorbent body 1 shown in FIG. 1 is situated between the first retaining sheet 2 and second retaining sheet 3 and includes a polymer absorbent 4 having a hydrophilic continuous skeleton and continuous pores, allowing it to absorb and retain liquid that has permeated through the first retaining sheet 2, as mentioned above.

The polymer absorbent 4 of the liquid absorbing member in the composite absorbent body 1 is bonded with the first retaining sheet 2 and second retaining sheet 3 by an adhesive such as a hot-melt adhesive, but the polymer absorbent does not need to be bonded with the retaining sheets in the composite absorbent body of the invention.

As mentioned above, the liquid absorbing member of the invention includes a polymer absorbent with characteristic liquid absorbing behavior, comprising a hydrophilic continuous skeleton and continuous pores. The polymer absorbent is described below.

According to the invention, the liquid absorbing member disposed between the first retaining sheet and second retaining sheet may also include another liquid-absorbing material, so long as it includes at least the polymer absorbent. That is, the liquid absorbing member may include the polymer absorbent alone as a liquid-absorbing material, or it may also include a liquid-absorbing material that is publicly known in the field, in addition to the aforementioned polymer absorbent. Such liquid-absorbing materials include hydrophilic fibers and superabsorbent polymers, and more specifically, cellulosic fibers including pulp fibers (such as ground pulp), cotton, rayon or acetate; granules composed of a superabsorbent polymer (SAP) such as sodium acrylate copolymer; or mixtures comprising any desired combinations of these.

For example, in the composite absorbent body 1' of the other embodiment shown in FIG. 2, the liquid absorbing member disposed between the first retaining sheet 2 and second retaining sheet 3 further includes a superabsorbent polymer 5 in addition to the particulate polymer absorbent 4 comprising a hydrophilic continuous skeleton and continuous pores and having the specified particle size.

According to the invention, the outer shape (the planar shape in the region where the liquid-absorbing material is present) and various dimensions and basis weight of the liquid absorbing member are not particularly restricted so long as the effect of the invention is not inhibited, and any desired outer shape or dimensions and basis weight may be employed depending on the desired liquid absorption, flexibility and strength.

(Hydrophilic Fiber Sheet)

The composite absorbent body of the invention may also have a hydrophilic fiber sheet 6 between the first retaining sheet 2 and the liquid absorbing member (that is, the polymer absorbent 4 and superabsorbent polymer 5), as in the composite absorbent body 1' of another embodiment shown in FIG. 2.

According to the invention, the hydrophilic fiber sheet used in the composite absorbent body is not particularly restricted so long as it does not interfere with the effect of the invention, and any hydrophilic fiber sheet may be employed according to the intended purpose and usage. Examples of such hydrophilic fiber sheets include hydrophilic nonwoven fabrics, woven fabrics and knitted fabrics. The hydrophilic fiber sheet may have a monolayer structure, or it may have a multilayer structure with two or more layers.

The type of constituent fibers of the hydrophilic fiber sheet is not particularly restricted, and examples include hydrophilic fibers such as cellulosic fibers or hydrophilicized thermoplastic resin fibers. Such fibers may be used alone, or two or more different types of fibers may be used in combination.

Examples of cellulosic fibers to be used as constituent fibers for the hydrophilic fiber sheet include natural cellulose fibers (such as cotton or other plant fibers), regenerated cellulose fibers, refined cellulose fibers and semi-synthetic cellulose fibers. Examples of thermoplastic resin fibers to be used as constituent fibers for the hydrophilic fiber sheet include fibers made of publicly known thermoplastic resins, including olefin-based resins such as PE and PP, polyester-based resins such as PET, and polyamide-based resins such as 6-nylon. Such resins may be used alone, or two or more resins may be used in combination.

According to the invention, the outer shape and various dimensions and basis weight of the hydrophilic fiber sheet are not particularly restricted so long as the effect of the invention is not inhibited, and any desired outer shape or dimensions and basis weight may be employed depending on the intended purpose and usage.

The polymer absorbent to be used in the composite absorbent body of the invention will now be explained in further detail.

[Polymer Absorbent]

According to the invention, the polymer absorbent is not particularly restricted so long as it comprises a hydrophilic continuous skeleton and continuous pores and exhibits characteristic liquid absorbing behavior whereby during absorption of a liquid, the liquid is taken up into the continuous pores after having been taken up into the continuous skeleton. Examples of such polymer absorbents include polymer compounds that are hydrolysates of crosslinked polymers of two or more monomers including at least a (meth)acrylic acid ester, and that have at least one hydrophilic group as a functional group. More specifically, such examples are polymer compounds that are hydrolysates of crosslinked polymers of a (meth)acrylic acid ester and a compound with two or more vinyl groups in the molecule, and that have at least a —COONa group. Such polymer absorbents may be organic porous bodies having at least one —COONa group in the molecule, and also having a —COOH group. The —COONa groups are approximately evenly distributed throughout the skeleton of the porous body.

If the polymer absorbent is a hydrolysate of a crosslinked polymer of a (meth)acrylic acid ester and a compound with two or more vinyl groups in the molecule, and contains at least one —COONa group, then the hydrophilic continuous skeleton will tend to stretch (i.e. expand) upon absorption of liquid such as aqueous solutions, and the continuous pores will also tend to widen, allowing more liquid to be more rapidly taken up into the continuous pores. This allows the composite absorbent body containing the polymer absorbent to exhibit more excellent absorption performance as an absorbent body.

As used herein, "(meth)acrylic acid ester" refers to an acrylic acid ester or methacrylic acid ester.

In a polymer absorbent formed by a hydrolysate of a crosslinked polymer comprising a (meth)acrylic acid ester and divinylbenzene, the hydrophilic continuous skeleton is formed of an organic polymer having at least a —COONa group, and between the skeleton it has communicating pores (continuous pores) serving as sites for absorption of liquid.

Since hydrolysis converts the —COOR group (carboxylic acid ester group) of the crosslinked polymer to a —COONa or —COOH group (see FIG. 2), the polymer absorbent may have a —COOR group.

The presence of —COOH groups and —COONa groups in the organic polymer forming the hydrophilic continuous skeleton can be confirmed by infrared spectrophotometry and quantitative analysis of the weakly acidic ion-exchange groups.

Figure 3:
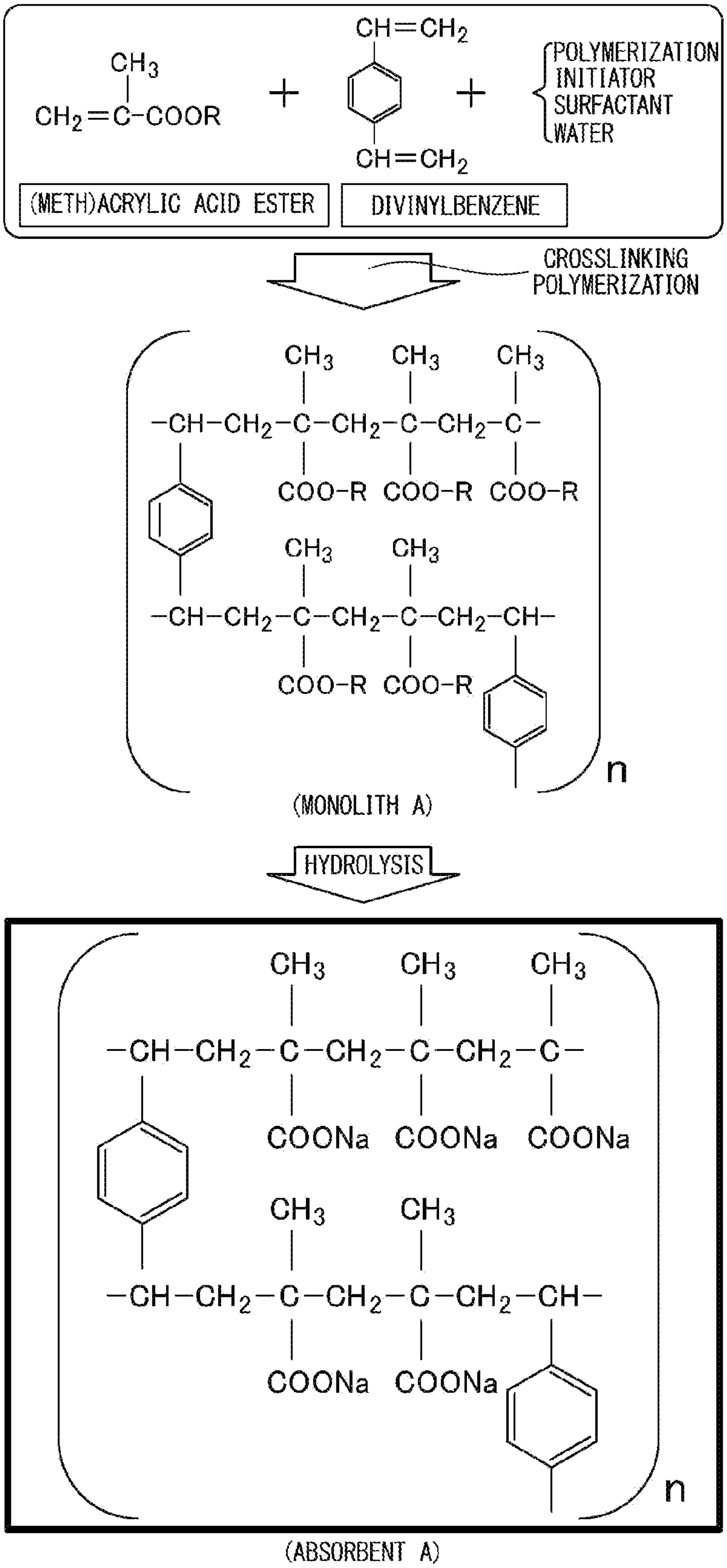
FIG. 3 is a diagram illustrating the process of producing absorbent A as an example of a polymer absorbent.

FIG. 3 is a diagram illustrating the process of producing absorbent A as an example of a polymer absorbent. FIG. 3 shows the constituent starting materials for polymerization at top, monolith A as a crosslinked polymer of a (meth) acrylic acid ester and divinylbenzene, at center, and absorbent A obtained by hydrolysis and drying treatment of monolith A, at bottom.

The following explanation concerns absorbent A, formed by hydrolysis of a crosslinked polymer of a (meth)acrylic acid ester and divinylbenzene, as an example of a polymer absorbent.

The polymer absorbent is not limited to absorbent A, and it may be a hydrolysate of a crosslinked polymer of a (meth)acrylic acid ester and a compound having two or more vinyl groups in the molecule, or a hydrolysate of a crosslinked polymer of two or more monomers including at least a (meth)acrylic acid ester.

If the polymer absorbent is a monolithic absorbent, however, an advantage is provided as the liquid can be rapidly absorbed and it is possible to deliver more reliably the liquid temporarily retained in the polymer absorbent to the SAP.

In the following explanation, "monolith A" refers to a "monolithic organic porous body", which is an organic porous body comprising a crosslinked polymer of a (meth) acrylic acid ester and divinylbenzene before hydrolysis.

The term "absorbent A" is a hydrolysate of the crosslinked polymer (monolith A) of the (meth)acrylic acid ester and divinylbenzene after hydrolysis and drying treatment. In the following explanation, "absorbent A" refers to the dry form.

The structure of absorbent A will be described first.

As explained above, absorbent A has a hydrophilic continuous skeleton and continuous pores. As shown in FIG. 3, absorbent A which is an organic polymer having a hydrophilic continuous skeleton, can be obtained by crosslinking polymerization of a (meth)acrylic acid ester as the polymerization monomer, and divinylbenzene as the crosslinking monomer, and hydrolysis of the obtained crosslinked polymer (monolith A).

The organic polymer forming the hydrophilic continuous skeleton has, as structural units, an ethylene group polymer residue (hereunder, "structural unit X") and a divinylbenzene crosslinking polymer residue (hereunder, "structural unit Y").

The ethylene group polymer residue (structural unit X) in the organic polymer forming the hydrophilic continuous skeleton has both —COONa groups, or both —COOH and —COONa groups, generated by hydrolysis of carboxylic acid ester groups. When the polymerization monomer is a (meth)acrylic acid ester, the polymer residue (structural unit X) of the ethylene group has a —COONa, —COOH group and ester group.

In the absorbent A, the ratio of divinylbenzene crosslinking polymer residue (structural unit Y) in the organic polymer forming the hydrophilic continuous skeleton may be 0.1 to 30 mol %, and preferably 0.1 to 20 mol %, with respect to the total structural units. For example, in absorbent A where butyl methacrylate is the polymerization monomer and divinylbenzene is the crosslinking monomer, the ratio of divinylbenzene crosslinking polymer residue (structural unit Y) in the organic polymer forming the hydrophilic continuous skeleton may be about 3 mol %, for example, and is preferably 0.1 to 10 mol %, and more preferably 0.3 to 8 mol %, with respect to the total structural units.

If the ratio of divinylbenzene crosslinking polymer residue in the organic polymer forming the hydrophilic continuous skeleton is 0.1 mol % or greater, the strength of absorbent A will be unlikely to decrease, and if the ratio of divinylbenzene crosslinking polymer residue is 30 mol % or lower, absorption of liquids to be absorbed will be unlikely to decrease.

The organic polymer forming the hydrophilic continuous skeleton in absorbent A may be composed entirely of structural unit X and structural unit Y, or it may have a structural unit other than structural unit X, and structural unit Y, i.e. a polymer residue of monomers other than (meth) acrylic acid ester and divinylbenzene, in addition to structural unit X and structural unit Y.

Examples of structural units other than structural unit X and structural unit Y include polymer residues of monomers such as styrene, α-methylstyrene, vinyltoluene, vinylbenzyl chloride, glycidyl (meth)acrylate, isobutene, butadiene, isoprene, chloroprene, vinyl chloride, vinyl bromide, vinylidene chloride, tetrafluoroethylene, (meth)acrylonitrile, vinyl acetate, ethylene glycol di(meth)acrylate, tripropyleneglycol di(meth)acrylate and trimethylolpropane tri(meth) acrylate.

The ratio of structural units other than structural unit X and structural unit Y in the organic polymer forming the hydrophilic continuous skeleton may be 0 to 50 mol %, and preferably 0 to 30 mol %, with respect to the total structural units.

The absorbent A preferably has a hydrophilic continuous skeleton thickness of 0.1 to 100 m. If the thickness of the hydrophilic continuous skeleton of absorbent A is 0.1 μm or greater, the spaces (pores) for uptake of liquid into the porous body will be unlikely to collapse during absorption, so that liquid absorption will be unlikely to decrease. A hydrophilic continuous skeleton thickness of 100 μm or lower will tend to result in an excellent absorption rate.

Since the pore structure of the hydrophilic continuous skeleton of absorbent A is an open-cell structure, the thickness of the continuous skeleton is evaluated by measuring the skeleton cross-section appearing in an electron microscope test piece. Since the continuous skeleton is formed at gaps where water (in the form of droplets) has been removed by dehydrating/drying treatment after hydrolysis, it usually has a polygonal shape. The thickness of the continuous skeleton is therefore the average of the diameters (m) of circumscribed circles in the polygonal cross-section. In rare cases the polygonal shapes will contain small open holes, and in such cases circumscribed circles surrounding the small holes are measured in the polygonal cross-sections.

The absorbent A also preferably has continuous pores with a mean diameter of 1 to 1000 m. If the mean diameter of the continuous pores of absorbent A is 1 μm or greater, the spaces (pores) for uptake of liquid into the porous body will be unlikely to collapse during absorption, so that the absorption rate will be unlikely to decrease. A continuous pore mean diameter of 1000 μm or lower will tend to result in an excellent absorption rate.

The mean diameter (m) of the continuous pores of absorbent A can be measured by the mercury intrusion method, using the maximum of the pore distribution curve obtained by mercury intrusion. Each sample for measurement of the continuous pore mean diameter is used after drying for 18 hours or longer in a vacuum dryer set to a temperature of 50° C., regardless of the ionic form of absorbent A. The final ultimate pressure is 0 Torr.

Figure 4:
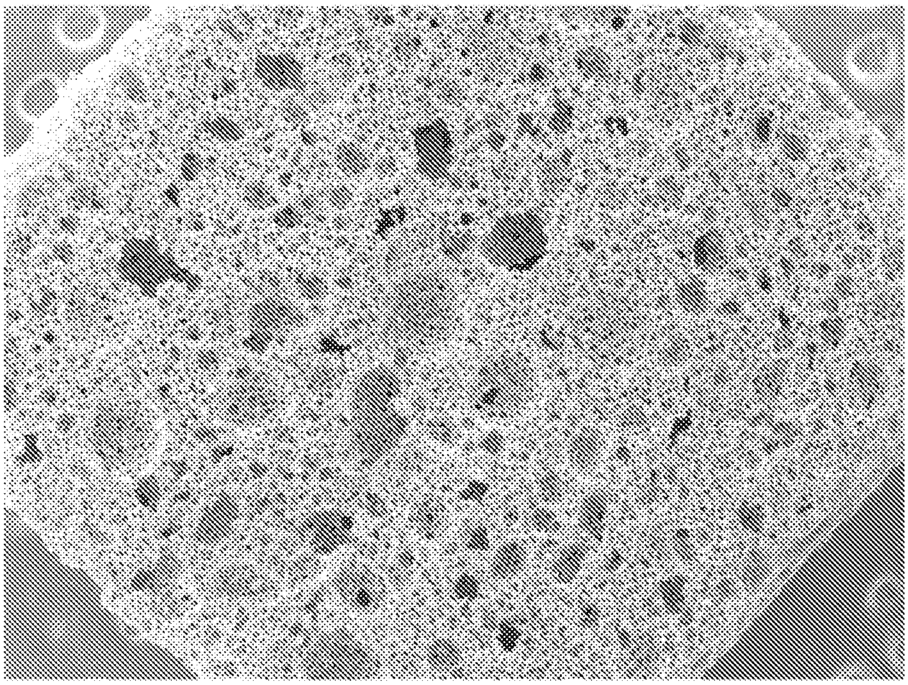
FIG. 4 is a SEM photograph of absorbent A at 50× magnification.
Figure 5:
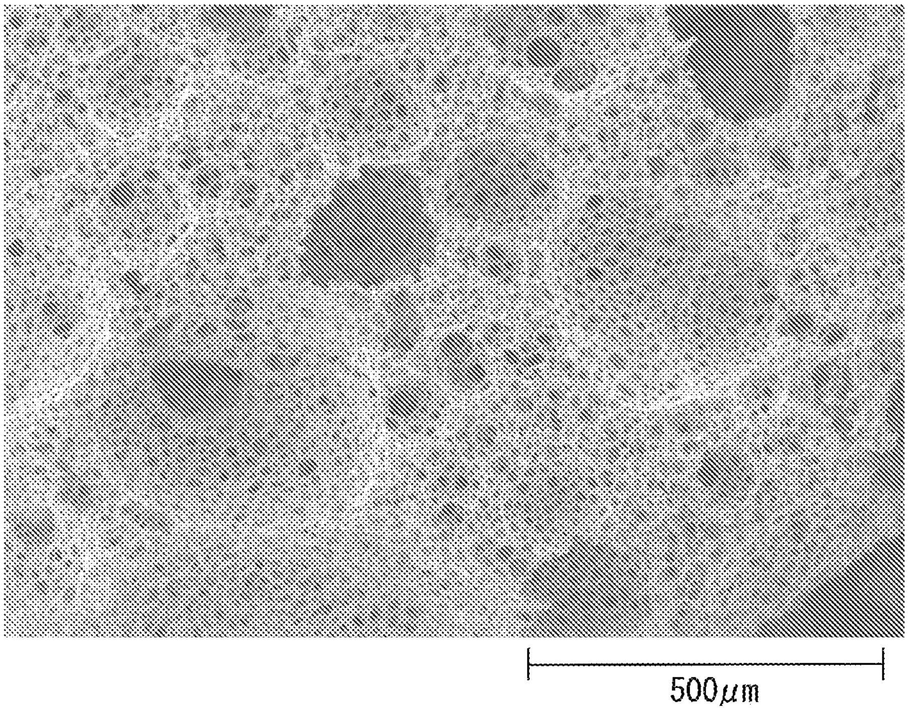
FIG. 5 is a SEM photograph of absorbent A at 100× magnification.
Figure 6:
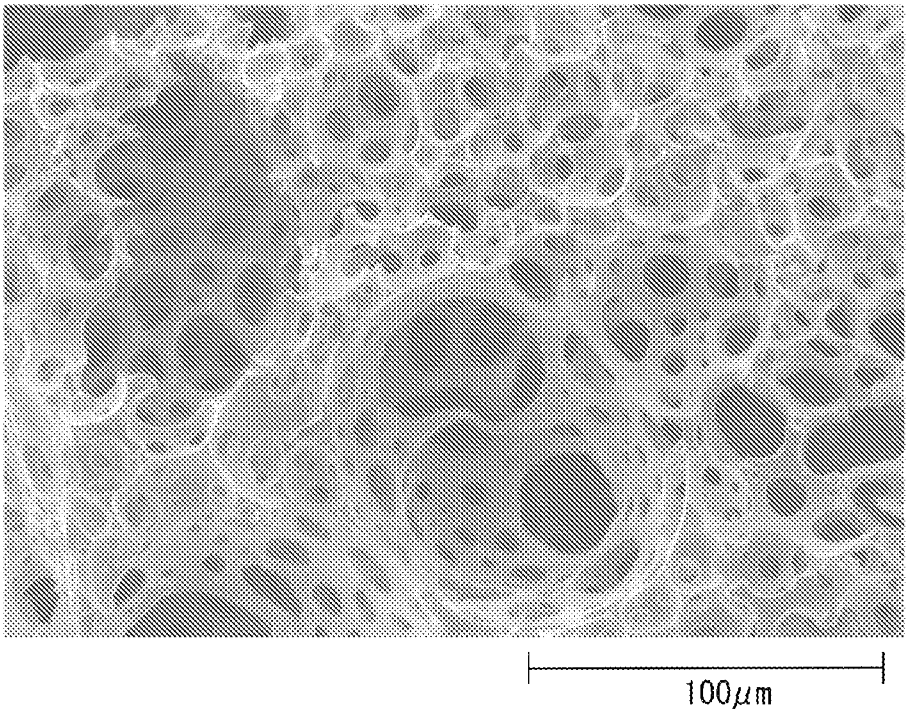
FIG. 6 is a SEM photograph of absorbent A at 500× magnification.
Figure 7:
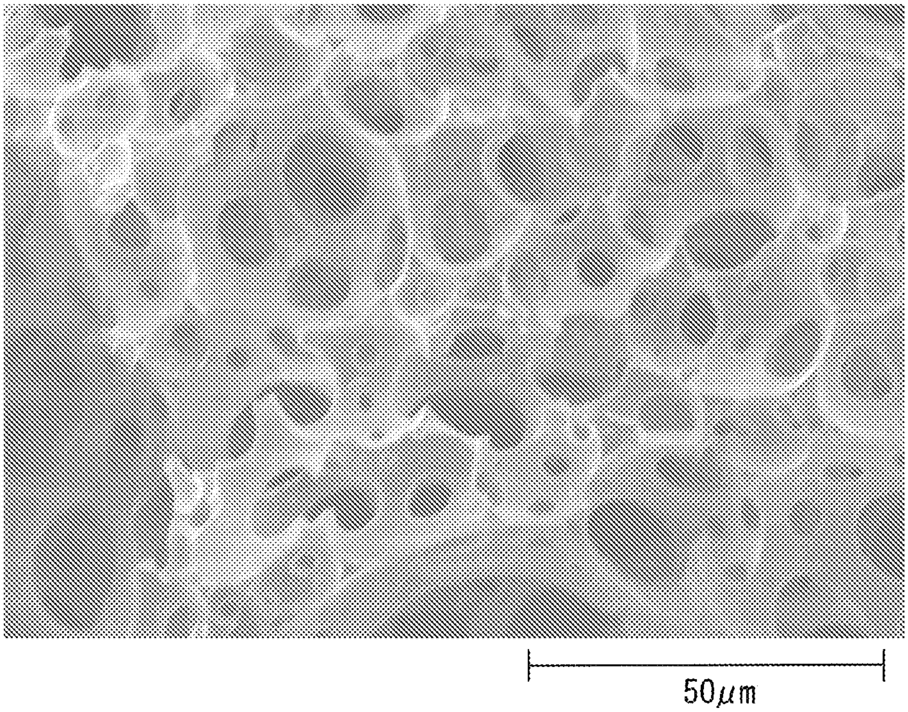
FIG. 7 is a SEM photograph of absorbent A at 1000× magnification.
Figure 8:
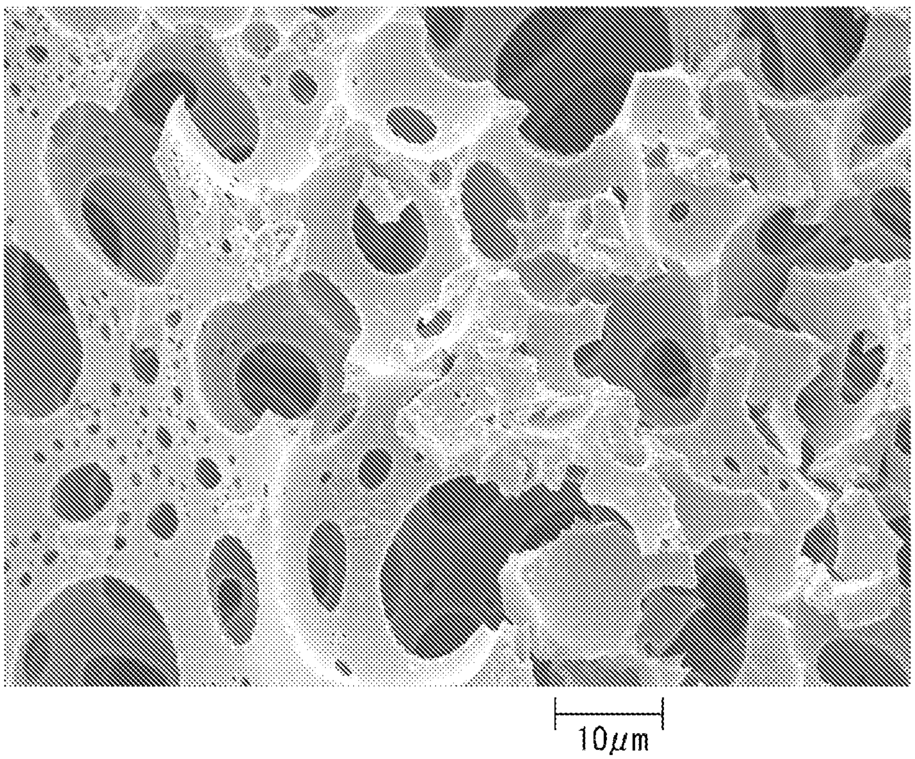
FIG. 8 is a SEM photograph of absorbent A at 1500× magnification.

FIG. 4 is a SEM photograph of absorbent A at 50× magnification, FIG. 5 is a SEM photograph of absorbent A at 100× magnification, FIG. 6 is a SEM photograph of absorbent A at 500× magnification, FIG. 7 is a SEM photograph of absorbent A at 1000× magnification, and FIG. 8 is a SEM photograph of absorbent A at 1500× magnification.

Absorbent A shown in FIG. 4 to FIG. 8 is an absorbent having butyl methacrylate as the polymerization monomer and divinylbenzene as the crosslinking monomer, each with a 2 mm-square cuboid structure.

Absorbent A shown in FIG. 4 to FIG. 8 also has numerous foamed macropores, with overlapping sections between the foamed macropores. Absorbent A has an open-cell construction with openings (mesopores) connecting the overlapping sections between the macropores, or in other words, it is an “open-cell structure” (continuous macropore structure).

The overlapping sections between the macropores are connected openings (mesopores) with a dry mean diameter of 1 to 1000 μm, preferably 10 to 200 μm and most preferably 20 to 100 m, the majority of which form an open pore structure. A dry mean diameter of 1 μm or greater for the mesopores will result in a more satisfactory absorption rate for liquid to be absorbed. A dry mean diameter of 1000 μm or smaller for the mesopores will tend to avoid brittleness for absorbent A.

The number of overlapping macropores are about 1 to 12 for each macropore, and about 3 to 10 for most.

If absorbent A has such an open-cell structure it will be possible to form homogeneous macropore groups and mesopore groups, while also significantly increasing the pore volume and area-to-weight ratio, compared to the particle-aggregate porous body described in Japanese Unexamined Patent Publication No. H08-252579.

The continuous pores of absorbent A are a plurality of mutually communicating pores. The total pore volume of pores in absorbent A is preferably 0.5 to 50 mL/g, more preferably 0.9 to 40 mL/g and even more preferably 2 to 30 mL/g. Since the total pore volume of absorbent A is 0.5 mL/g or greater, sufficient pore volume can be ensured for absorbent A, thus making it possible to ensure an adequate amount of liquid absorption. During absorption, this can also help prevent collapse of the spaces (pores) for uptake of liquids into the porous body, and can help prevent reduction in the amount and rate of liquid absorption. If the total pore volume of absorbent A is 50 mL/g or lower, on the other hand, the strength of absorbent A will be unlikely to decrease.

The total pore volume can be measured by the mercury intrusion method. The measuring sample for total pore volume is used after drying for 18 hours or longer in a vacuum dryer set to a temperature of 50° C., regardless of the ionic form of absorbent A. The final ultimate pressure is 0 Torr. The mercury intrusion method yields a cumulative (integrated) pore volume distribution (relationship between pore radius and cumulative pore volume) or a log differential pore volume distribution (relationship between pore radius and log differential pore volume), allowing calculation of the total pore volume (mL/g), the mean pore radius (m), the maximum pore radius (μm), the pore volume (mL/g) and ratio (%) of pores at or above/below a predetermined pore radius, and the coefficient of variation of the pore volume. The maximum pore size (m) is the pore radius of pores representing the maximum pore volume. The pore volume (mL/g) at each pore radius is determined using the log differential pore volume (mL/g) in the log differential pore volume distribution.

The ratio of the pore volume of pores with pore radii of 1 μm or greater among the pores of absorbent A is 90% or greater, preferably 93% or greater and more preferably 95% or higher of the pore volume of all of pores (total pore volume). Since the ratio of pore volume of pores with pore radii of 1 μm or greater is 90% or greater, even though it will be difficult for liquid components to be taken up into pores with relatively small pore radii, such as pore radii of less than 1 μm, without being taken up by those pores, it will still be possible to ensure an adequate amount of liquid absorption. As a result, reduction in liquid absorption in proportion to pore volume can be inhibited, allowing excellent absorption performance to be obtained.

Among the pores of absorbent A, the ratio of the pore volume of pores with pore radii of 0.005 μm or smaller is preferably less than 10% of the pore volume of all of pores (total pore volume), and the ratio of the pore volume of pores with pore radii of 0.05 μm or smaller is preferably less than 10% of the pore volume of all of pores (total pore volume). With absorbent A, the ratio of the pore volume of pores with extremely small pore radii which are less able to absorb liquids, such as pore radii of 0.005 μm or smaller, is very low, while the ratio of the pore volume of pores of large pore radii which are able to absorb liquids, such as pore radii of 1 μm or greater, is very large (≥90%). This allows the pores of absorbent A to be effectively used for liquid absorption, to ensure an adequate amount of liquid absorption.

Among the pores of absorbent A, the pore radii of pores representing the maximum value of the pore volume (equal to or greater than 0.5 μm) is preferably 500 μm or lower, more preferably 300 μm or lower and even more preferably 150 μm or lower. If the pore radius at the maximum value of the pore volume is 500 μm or lower, then it is possible to prevent disintegration (collapse) of the continuous skeleton structure of absorbent A, thus helping to obtain an excellent absorption rate and stably ensuring an adequate amount of liquid absorption. If the pore radius at the maximum value of the pore volume is 500 μm or greater, then the structure of the continuous skeleton may not be maintained and may collapse during liquid absorption.

The coefficient of variation of the pore distribution (pore volume) of pores with pore radii of 1 μm or greater among the pores of absorbent A may be 1.4 or smaller. Since the coefficient of variation of the pore distribution is 1.4 or smaller, there is less variation in pore radius with respect to the average pore radius, resulting in a sharp peak representing the pore distribution near the average pore radius. Absorbent A can therefore absorb liquids approximately evenly in all directions over the entire surface. This allows the pores of the polymer absorbent to be effectively used for liquid absorption, to ensure an adequate amount of liquid absorption.

The coefficient of variation of the pore distribution (pore volume) of pores with pore radii of 1 μm or greater among the pores of absorbent A may also be larger than 1.4. Since the coefficient of variation of the pore distribution is larger than 1.4 in this case, there is high variation in pore radius with respect to the average pore radius, resulting in a broad peak representing the pore distribution near the average pore radius. In other words, absorbent A has both pores with small pore radii and pores with large pore radii. Consequently, capillary action takes place more easily in the pores with small pore radii, resulting in a faster liquid absorption rate, while the liquid absorption volume tends to increase in the pores with large pore radii. As a result, a synergistic effect is exhibited by both, allowing absorbent A to instantly absorb large amounts of liquid into the pores.

If the peak represented by the pore distribution is broad for the pores of absorbent A, then for the pore radii corresponding to the local maximum value of the pore volume in the pore distribution curve, the region on a side of larger pore radii may be broader than the region on a side of smaller pore radii. In this case, absorbent A has a structure with more pores of large pore size than pores with small pore radii. By having more pores with large pore radii, therefore, the liquid absorption volume tends to increase, allowing absorption of larger amounts of liquid into the pores.

Even if the peak represented by the pore distribution is broad for the pores of absorbent A, the region on the side of smaller pore radii may be broader than the region on the side of larger pore radii, for the pore radii corresponding to the maximum value of the pore volume in the pore distribution curve. In this case, absorbent A has a structure with more pores of small pore size than pores with large pore radii. By having more pores with small pore radii, capillary action tends to take place more easily, thus further increasing the liquid absorption rate and allowing more instant absorption of liquid into the pores.

The pores of absorbent A may also have at least two local maximum values of the pore volume in the pore distribution curve. In this case, absorbent A has both pores with the prescribed small pore radii and pore radii in that vicinity, and pores with the prescribed larger pore radii and pore radii in that vicinity. Consequently, capillary action takes place more easily in the pores with relatively small pore radii, resulting in a faster liquid absorption rate, while the liquid absorption volume tends to be greater in the pores with relatively large pore radii. As a result, a synergistic effect is exhibited by both, allowing the polymer absorbent to instantly absorb large amounts of liquid into the pores.

When the pores of absorbent A have two local maximum values of the pore volume, the two local maximum values of the pore volume in the pore distribution curve may be such that the local maximum value for relatively small pore radii is larger than the local maximum value for relatively large pore radii. In this case, absorbent A will have more pores of small pore radii than pores with large pore radii. By having more pores with small pore radii, the capillary action tends to take place more easily, thus further increasing the liquid absorption rate and allowing more instant absorption of liquid into the pores.

When the pores of absorbent A have two local maximum values of the pore volume, the two local maximum values of the pore volume in the pore distribution curve may also be such that the local maximum value for relatively small pore radii is smaller than the local maximum value for relatively large pore radii. In this case, absorbent A will have more pores of large pore radii than pores with small pore radii. By having more pores with large pore radii, the liquid absorption volume tends to increase, allowing absorption of larger amounts of liquid component into the pores.

The bulk density in the pores of absorbent A is preferably 0.07 to 0.6 g/cm$^3$, more preferably 0.1 to 0.4 g/cm$^3$ and even more preferably 0.15 to 0.35 g/cm$^3$. In this case, the liquid absorption rate (DW) performance may be 6 mL/30 sec or greater, more preferably 10 mL/30 sec or greater and even more preferably 12 mL/30 sec or greater, as explained below. In other words, because the liquid absorption rate is faster, the polymer absorbent can more instantly absorb liquid into the pores.

<Method of Measuring Liquid Absorption Rate (DW)>

Figure 12:
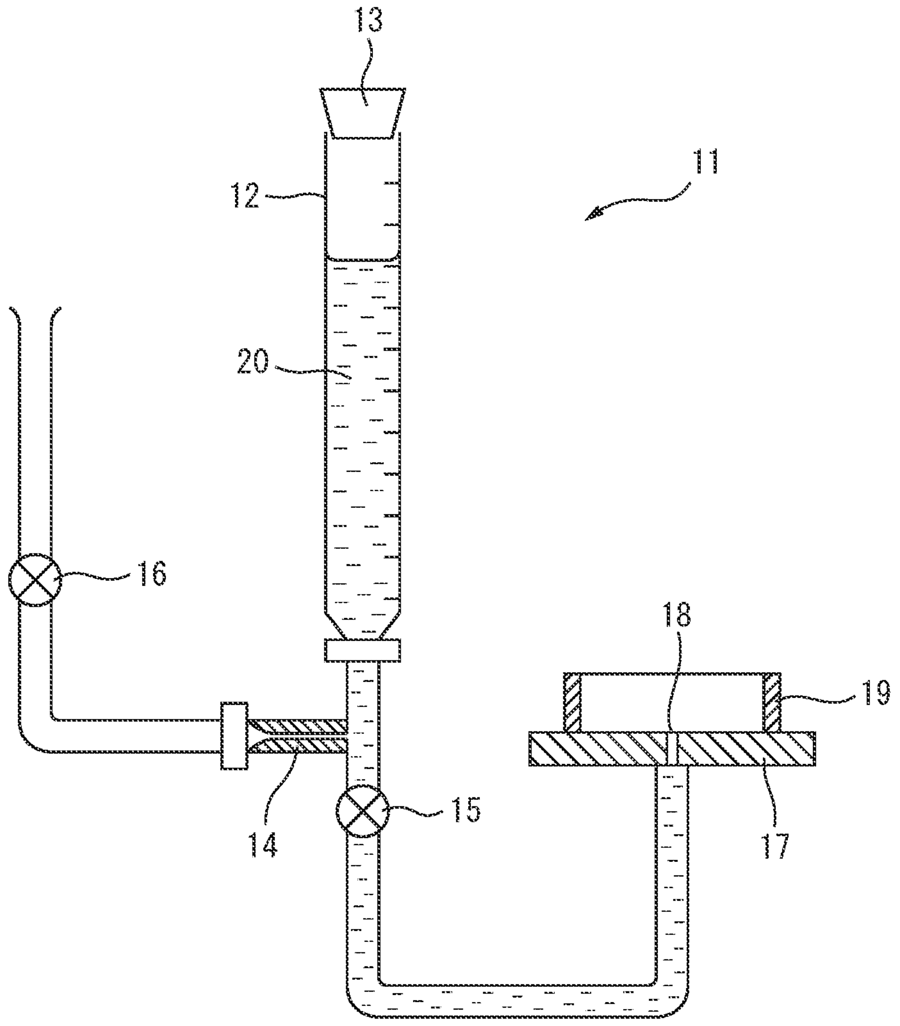
FIG. 12 is a schematic diagram of a measuring apparatus to be used in an unpressurized DW method.

The liquid absorption rate of the absorbent is measured by an unpressurized DW (Demand Wettability) method. FIG. 12 is a schematic diagram of a measuring apparatus to be used in an unpressurized DW method. For the measurement there was used a DW (Demand Wettability) device 11 by Taiyo Create Co., Ltd. As shown in the drawing, the DW apparatus 11 comprises a burette 12 (50 ml scale capacity, 86 cm length, 1.05 cm inner diameter), a rubber stopper 13, an air inlet tubule (tip inner diameter: 3 mm) 14, a cock 15, a cock 16, a measuring stage 17, a liquid outlet (inner diameter: 3 mm) 18, a cylinder 19 and a test solution 20. A tube (7 mm inner diameter) was attached between the burette 12 and the measuring stage 17. The test solution used is a 0.9% sodium chloride aqueous solution. The measurement is conducted in an atmosphere of 25° C.×50% RH (in a steady temperature and humidity room).

The specific measurement procedure is as follows.

(1) The test solution 20 is added to higher than point 0 (the top of the burette 12 scale (0 ml line)), with both cocks 15, 16 of the DW apparatus 11 closed off, and the rubber stopper 13 is placed over the burette 12, to seal it.

(2) After placing filter paper on the liquid outlet 18 of the measuring stage 17, both cocks 15, 16 are opened, and the liquid level is matched to point 0 while suctioning out the liquid flowing out from the liquid outlet 18 with the filter paper. After preparation, the cocks 15, 16 are closed.

(3) A 100% wood pulp tissue (basis weight: 15±1 gsm, thickness measured by nonwoven fabric thickness gauge with a measuring pressure of 3 g/cm$^2$: 0.1±0.02 mm) is set on the measuring stage 17 with the liquid outlet 18 at the center.

(4) The cylinder 19 having a diameter of 30 mm is placed at the center section of the tissue, and the test object (polymer absorbent) is placed inside it with the liquid outlet 18 at the center. The test object is placed in the cylinder 19 and peripherally constrained by the cylinder 19.

(5) The cocks 15, 16 are opened to initiate absorption of the test solution 20 by the test object, and the time when the first bubble introduced from the air inlet tubule 14 reaches the liquid surface of the test solution 20 in the burette 12 (the point at which the liquid surface of the test solution 20 in the burette 12 falls) is recorded as the measurement start time.

(6) The amount of reduction in the test solution 20 in the burette 12 (the amount of test solution 20 absorbed by the test object) M (ml) is continuously read off.

(7) The absorption by the test object after elapse of a predetermined time from the start of liquid absorption (30 seconds for this embodiment) is calculated by the DW method as:

Absorption (ml/g)=M (ml)/(weight (g) of test object (polymer absorbent)).

The state where absorbent A has contacted liquid will be described below, the description also applying to contact between liquid and the liquid absorbing member or composite absorbent body 4 that includes absorbent A. Since the mass of the absorbed liquid is approximately proportional to the liquid volume, the mass of the liquid will be referred to below simply as “liquid volume”.

The continuous pores of absorbent A shown in FIG. 4 to FIG. 8 are holes mutually connecting multiple pores (holes), the numerous holes being outwardly visible to the naked eye. When liquid contacts with absorbent A comprising such numerous holes, the hydrophilic continuous skeleton immediately takes up a portion of the liquid by osmotic pressure, thereby stretching (i.e., expanding). Stretching of the continuous skeleton takes place in approximately all directions. The absorbent A that has thus enlarged by absorption of a certain amount of liquid is then able to absorb an additional amount of liquid in the enlarged continuous pores, by capillary movement. Absorbent A also exhibits characteristic liquid absorbing behavior, whereby during absorption of liquid, the liquid is taken up and absorbed into the continuous pores after having been taken up into the hydrophilic continuous skeleton.

Since the liquid that has been absorbed in the hydrophilic continuous skeleton of absorbent A is less easily released (dissociated) from the continuous skeleton while the liquid that has been absorbed in the continuous pores is more readily dissociated, the liquid absorbed in the continuous pores inside the composite absorbent body is released and delivered to the highly liquid retaining superabsorbent polymer (SAP), thus being firmly retained in the SAP.

Of the liquid volume absorbed into the continuous skeleton of absorbent A and the liquid volume absorbed into the continuous pores, the liquid volume released (dissociated) from absorbent A by centrifugation (150 G/90 sec), of the total liquid volume absorbed by absorbent A, is the liquid volume absorbed into the continuous pores, while the rest of the liquid volume (that is, the liquid volume that was not dissociated from absorbent A by centrifugation) is the liquid volume absorbed into the continuous skeleton.

Of the liquid absorbed into absorbent A, the amount of liquid retained in the pores is greater than the amount of liquid absorbed into the hydrophilic continuous skeleton. Since most of the liquid absorption by absorbent A takes place by retaining liquid in the pores by capillary movement, a larger void percentage, as the ratio of volume of pore voids (total pore volume) (the volume of pore voids with respect to volume of absorbent A), allows greater absorption of liquid. The void percentage is preferably 85% or greater.

For example, the void percentage of absorbent A in FIG. 4 to FIG. 8 is determined as follows.

First, the area-to-weight ratio of absorbent A obtained by the mercury intrusion method is 400 μm$^2$/g, and the pore volume is 15.5 mL/g. A pore volume of 15.5 mL/g means that the volume of pores in 1 g of absorbent A is 15.5 mL.

Assuming a specific gravity of 1 g/mL for absorbent A, the volume occupied by pores in 1 g of absorbent A (the pore volume) is 15.5 mL, the volume of 1 g of absorbent A being 1 mL.

Thus, the total volume of 1 g of absorbent A is 15.5+1 (mL), the pore volume ratio of which is the void percentage, and therefore the void percentage of absorbent A is 15.5/(15.5+1)×100≈94%.

According to the invention, absorbent A (the polymer absorbent) comprising the hydrophilic continuous skeleton and continuous pores is suitable for application in a composite absorbent body in the form of particulates or a sheet, for example.

As mentioned above, the polymer absorbent has characteristic liquid absorbing behavior whereby, during absorption of liquid, the liquid is taken up into the continuous pores after having been taken up into the hydrophilic continuous skeleton, and therefore a large amount of liquid can be instantly absorbed, the absorbed liquid (primarily the liquid absorbed into the continuous pores) also being delivered into the SAP which has high water retention capacity, and being firmly held in the SAP. This allows the composite absorbent body employing the polymer absorbent to exhibit high absorption performance as an absorbent body.

Liquid absorption by the polymer absorbent can be measured according to <Method of measuring liquid absorption of polymer absorbent> below.

<Method of Measuring Liquid Absorption of Polymer Absorbent>

(1) A 1 g portion of sample to be measured (polymer absorbent) is encapsulated in a mesh bag cut to 10 cm square (N-N0255HD 115 by NBC Meshtec, Inc. (standard width:

115 cm, 255 mesh/2.54 cm, opening: 57 μm, filament diameter: 43 μm, thickness: 75 μm). The mass (g) of the mesh bag is measured in advance. The measurement is carried out under conditions with a temperature of 25° C. and a humidity of 60%. When the measuring sample (polymer absorbent) used is to be collected from a sanitary product, it can be obtained according to <Measuring sample (polymer absorbent) collection method> below.

(2) The sample-encapsulating mesh bag is immersed in a 0.9% aqueous sodium chloride solution for 1 hour.

(3) The mass (g) of the mesh bag is measured after hanging liquid draining for 5 minutes.

(4) The total of the mass of the sample (=1 g) and the mesh bag is subtracted from the mass of the drained mesh bag measured in (3) to calculate the liquid absorption (g) of the sample, and the liquid absorption is then divided by the mass of the sample (=1 g) to obtain the liquid absorption per unit mass (g/g) for the sample (polymer absorbent).

When the measuring sample (polymer absorbent) used is to be collected from a composite absorbent body product, it can be obtained by the following <Measuring sample (polymer absorbent) collection method>.

<Measuring Sample (Polymer Absorbent) Collection Method>

(1) The retaining sheet is peeled from the composite absorbent body product to expose the liquid absorbing member.

(2) The material to be measured (polymer absorbent) is dropped out from the exposed liquid absorbing member and materials other than the (particulate) material to be measured (for example, pulp and synthetic resin fibers) are removed using forceps.

(3) A microscope or simple magnifying lens is used as magnified observation means for observation at a magnification allowing discrimination of SAP differences or a magnification allowing visualization of pores in the porous body, while using the forceps to collect the material to be measured. The magnification of the simple magnifying lens is not particularly restricted so long as it is a magnification allowing visualization of the pores in the porous body, and it may be 25× or 50× magnification, for example.

(4) The collected material to be measured is used as a sample for measurement according to different measuring methods.

The method for producing the polymer absorbent will now be described in detail for the aforementioned absorbent A as an example.

[Method for Producing Polymer Absorbent]

As shown in FIG. 3, absorbent A can be obtained by a crosslinking polymerization step and a hydrolysis step. The steps will now be explained in detail.

(Crosslinking Polymerization Step)

First, an oil-soluble monomer for crosslinking polymerization, a crosslinkable monomer, a surfactant and water, with a polymerization initiator as necessary, are mixed to obtain a water-in-oil emulsion. The water-in-oil emulsion is an emulsion having an oil phase as the continuous phase which contains dispersed water droplets.

For absorbent A, as shown at top of FIG. 3, crosslinking polymerization is carried out using the (meth)acrylic acid ester butyl methacrylate as the oil-soluble monomer, divinylbenzene as the crosslinkable monomer, sorbitan monooleate as the surfactant and isobutyronitrile as the polymerization initiator, to obtain monolith A.

Specifically, for absorbent A, as indicated at top of FIG. 3, 9.2 g of t-butyl methacrylate as the oil-soluble monomer, 0.28 g of divinylbenzene as the crosslinkable monomer, 1.0 g of sorbitan monooleate (SMO) as the surfactant and 0.4 g of 2,2'-azobis(isobutyronitrile) as the polymerization initiator are mixed and homogeneously dissolved.

The mixture of t-butyl methacrylate/divinylbenzene/SMO/2,2'-azobis(isobutyronitrile) is then added to 180 g of purified water, and the resulting mixture is stirred under reduced pressure using a vacuum stirring/degassing mixer (product of EMI) as a planetary stirrer, to obtain a water-in-oil emulsion.

The emulsion is rapidly transferred to a reactor and sealed, and then polymerization is carried out under stationary conditions of 60° C., 24 hours. Upon completion of polymerization, the contents are removed out, extracted with methanol, and dried under reduced pressure, to obtain monolith A having a continuous macropore structure. Observation of the internal structure of monolith A by SEM showed that monolith A had an open-cell structure and a continuous skeleton thickness of 5.4 μm. The mean diameter of the continuous pores measured by mercury intrusion was 36.2 μm, and the total pore volume was 15.5 mL/g.

The divinylbenzene content with respect to the total monomer is preferably 0.3 to 10 mol % and more preferably 0.3 to 5 mol %. The ratio of divinylbenzene with respect to the total of butyl methacrylate and divinylbenzene is preferably 0.1 to 10 mol % and more preferably 0.3 to 8 mol %. For absorbent A, the ratio of butyl methacrylate with respect to the total of butyl methacrylate and divinylbenzene is 97.0 mol %, and the ratio of divinylbenzene is 3.0 mol %.

The amount of surfactant added can be set according to the type of oil-soluble monomer and the desired size of the emulsion particles (macropores), being preferably in the range of about 2 to 70% with respect to the total amount of the oil-soluble monomer and surfactant.

For control of the foamed form and size of monolith A, an alcohol such as methanol or stearyl alcohol; a carboxylic acid such as stearic acid; a hydrocarbon such as octane, dodecane or toluene; or a cyclic ether such as tetrahydrofuran or dioxane may be added into the polymerization system.

The mixing method for formation of the water-in-oil emulsion is not particularly restricted, and for example, it may be a method of mixing each of the components all at once, or a method of mixing each of the components after having separately and homogeneously dissolved the oil-soluble monomer, surfactant and oil-soluble polymerization initiator as the oil-soluble components, and the water and water-soluble polymerization initiator, as the water-soluble components.

The mixer used to form the emulsion is also not particularly restricted, and any apparatus such as an ordinary mixer, homogenizer or high-pressure homogenizer may be employed depending on the desired particle size for the emulsion, or a planetary stirrer may be used, wherein the material to be treated is placed in a mixing vessel and the material is stirred and mixed by rotation of the mixing vessel while it revolves around a revolution axis in an inclined state.

The mixing conditions are also not particularly restricted, and the stirring rotational speed and stirring time may be arbitrarily set depending on the desired particle size for the emulsion. A planetary stirrer as described above can form homogeneous water droplets in a W/O emulsion, and the mean diameter may be set within a wide range.

The polymerization conditions for the water-in-oil emulsion may be any of various conditions set depending on the type of monomer or initiator. For example, when using azobisisobutyronitrile, or benzoyl peroxide or potassium persulfate as the polymerization initiator, thermal polymerization may be carried out in a sealed vessel under an inert atmosphere at a temperature of 30 to 100° C. for 1 to 48 hours, or when using hydrogen peroxide-ferrous chloride or sodium persulfate-acidic sodium sulfite as the polymerization initiator, polymerization may be carried out in a sealed vessel under an inert atmosphere at a temperature of 0 to 30° C. for 1 to 48 hours.

Upon completion of polymerization, the contents may be removed and subjected to Soxhlet extraction with a solvent such as isopropanol to remove the unreacted monomer and residual surfactant, to obtain monolith A shown at center in FIG. 3.

(Hydrolysis Step)

A subsequent step of hydrolysis of monolith A (crosslinked polymer) to obtain absorbent A (hydrolysis step) will now be explained.

First, monolith A is immersed in zinc bromide-added dichloroethane and stirred at 40° C. for 24 hours, contacted with methanol, 4% hydrochloric acid, 4% aqueous sodium hydroxide and water in that order for hydrolysis, and then dried to obtain absorbent A in block form. The block absorbent A is pulverized to the desired size to obtain particulate absorbent A. The form of absorbent A is not limited to being particulate, and for example, it may be formed into a sheet either during or after drying.

The hydrolysis method for monolith A is not particularly restricted, and any of various methods may be applied. For example, it may be a method of contacting an aromatic solvent such as toluene or xylene, a halogen-based solvent such as chloroform or dichloroethane, an ether-based solvent such as tetrahydrofuran or isopropyl ether, an amide-based solvent such as dimethylformamide or dimethyl acetamide, an alcohol-based solvent such as methanol or ethanol, or a carboxylic acid-based solvent such as acetic acid or propionic acid, or water, as a solvent, with a strong base such as sodium hydroxide, or a method of contacting with a hydrohalic acid such as hydrochloric acid, a Bronsted acid such as sulfuric acid, nitric acid, trifluoroacetic acid, methanesulfonic acid or p-toluenesulfonic acid, or a Lewis acid such as zinc bromide, aluminum chloride, aluminum bromide, titanium(IV) chloride, cerium chloride/sodium iodide or magnesium iodide.

The (meth)acrylic acid ester in the polymerization material for the organic polymer that is to form the hydrophilic continuous skeleton of absorbent A is not particularly restricted, but it is preferably a C1-C10 (1 to 10 carbon atom) alkyl ester of (meth)acrylic acid, and most preferably a C4 (4 carbon atom) alkyl ester of (meth)acrylic acid.

C4 alkyl esters of (meth)acrylic acid include t-butyl (meth)acrylate esters, n-butyl (meth)acrylate esters and isobutyl (meth)acrylate esters.

The monomers to be used for crosslinking polymerization may be a (meth)acrylic acid ester and divinylbenzene alone, or they may include monomers other than a (meth)acrylic acid ester and divinylbenzene, in addition to the (meth) acrylic acid ester and divinylbenzene.

In the latter case, other monomers are not particularly restricted and include, for example, styrene, α-methylstyrene, vinyltoluene, vinylbenzyl chloride, glycidyl (meth) acrylate, 2-ethylhexyl (meth)acrylate, isobutene, butadiene, isoprene, chloroprene, vinyl chloride, vinyl bromide, vinylidene chloride, tetrafluoroethylene, (meth)acrylonitrile, vinyl acetate, ethylene glycol di(meth)acrylate and trimethylolpropane tri(meth)acrylate.

The ratio of monomers other than the (meth)acrylic acid ester and divinylbenzene in the total monomers used for crosslinking polymerization is preferably 0 to 80 mol % and more preferably 0 to 50 mol %.

The surfactant is not limited to sorbitan monooleate mentioned above and may be any one that can form a water-in-oil (W/O) emulsion when mixed with the crosslinking polymerization monomer and water. Examples of surfactants include nonionic surfactants such as sorbitan monolaurate, sorbitan monopalmitate, sorbitan monostearate, sorbitan trioleate, polyoxyethylene nonylphenyl ether, polyoxyethylene stearyl ether and polyoxyethylene sorbitan monooleate, anionic surfactants such as potassium oleate, sodium dodecylbenzenesulfonate and dioctylsodium sulfosuccinate, cationic surfactants such as distearyldimethylammonium chloride, and amphoteric surfactants such as lauryldimethyl betaine. Such surfactants may be used alone, or two or more may be used in combination.

The polymerization initiator used may be a compound that generates radicals under heat or photoirradiation. The polymerization initiator may be water-soluble or oil-soluble, and examples include azobis(4-methoxy-2,4-dimethylvaleronitrile), azobisisobutyronitrile, azobisdimethylvaleronitrile, azobiscyclohexanenitrile, azobiscyclohexanecarbonitrile, azobis(2-methylpropionamidine) dihydrochloride, benzoyl peroxide, potassium persulfate, ammonium persulfate, hydrogen peroxide-ferrous chloride, sodium persulfate-acidic sodium sulfite and tetramethylthiuram disulfide. Depending on the system, however, polymerization may proceed by heating alone or photoirradiation alone without addition of a polymerization initiator, and in such cases there is no need to add a polymerization initiator.

EXAMPLES

The present invention will now be explained showing Examples below. However, the present invention is not limited to the Examples in any way.

(A) Sample (a) Pore Distribution

The polymer absorbents of the invention produced by the production method described above were prepared as samples for Examples 1 to 5, and Infinity Particles were prepared as samples for Comparative Examples 1 to 2. For the samples of Examples 1 to 5, the surfactant/monomer ratios (wt %) and stirring times (min) were changed during formation of the water-in-oil emulsions in the production method. Infinity Particles are an absorbent by P&G Corp., which have a structure (foam structure) similar to a polymer absorbent, but differing from a polymer absorbent by having no function of expanding by absorption of liquid.

(b) Relationship Between Bulk Density and Liquid Absorption Rate

For the samples of the Examples, the ethanol immersion and drying conditions were changed to prepare samples with different bulk densities. Specifically, after sufficiently immersing the dried polymer absorber in a 40% ethanol aqueous solution, and then repeatedly removing the supernatant liquid and adding ethanol to adjust the ethanol solution to the predetermined concentration and again sufficiently immersing, the wetted polymer absorber was filtered and dried under reduced pressure overnight at 50° C. to obtain polymer absorbers with different bulk densities.

(B) Evaluation (a) Pore Distribution

In the mercury intrusion method, a cumulative (integrated) pore volume distribution (relationship between pore radius and cumulative pore volume) or a log differential pore volume distribution (relationship between pore radius and log differential pore volume) was determined for each sample, to calculate the total pore volume (mL/g), the mean pore radius (m), the maximum pore radius (m), the (ratio of) pore volume of pores at or above/below a predetermined pore radius, and the coefficient of variation of the pore volume.

(b) Relationship Between Bulk Density and Liquid Absorption Rate

The liquid absorption rate (DW) of each sample was measured to examine the relationship between the bulk density and liquid absorption rate (DW) of each sample.

(C) Evaluation Results (a) Pore Distribution

Figure 9:
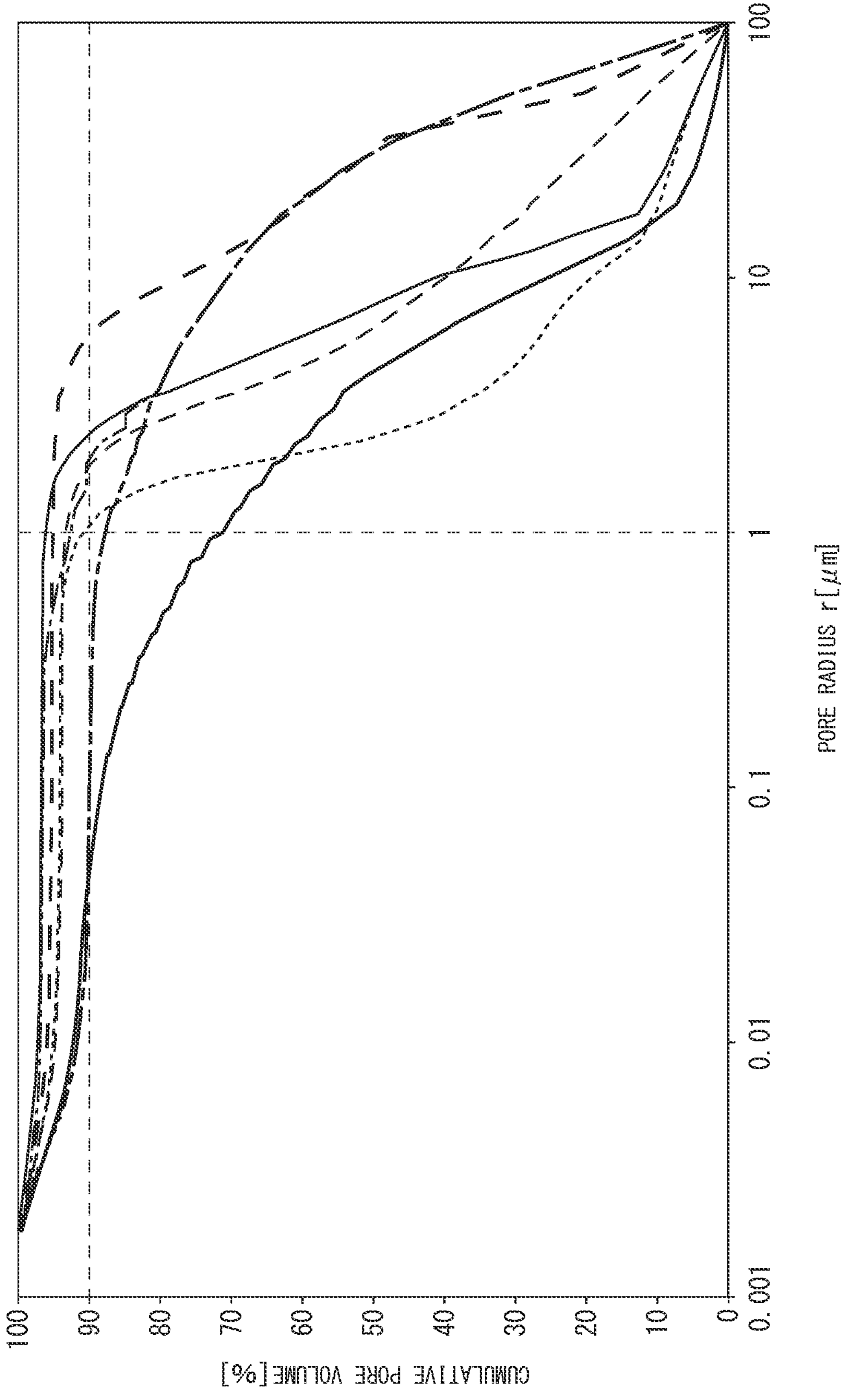
FIG. 9 is a graph showing the relationship between pore radius and cumulative pore volume, for absorbent A.
Figure 10:
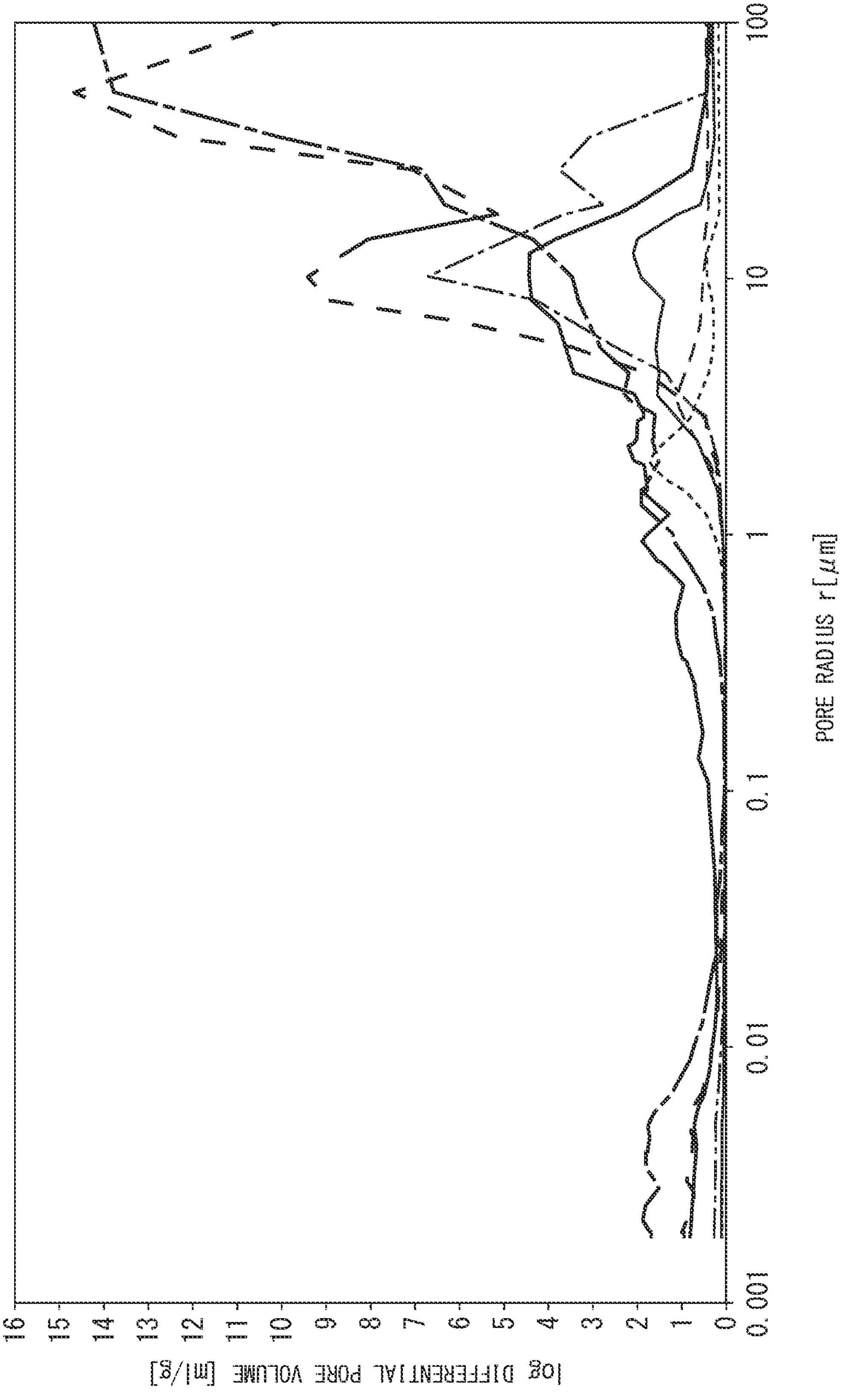
FIG. 10 is a graph showing the relationship between pore radius and differential pore volume, for absorbent A.

The measurement results are shown in FIG. 9 and FIG. 10, and the values are summarized in Table 1. FIG. 9 shows the obtained cumulative (integrated) pore volume distribution, i.e., the relationship between the pore radius (abscissa) and the cumulative pore volume (ordinate), and FIG. 10 shows the obtained log differential pore volume distribution, i.e., the relationship between the pore radius (abscissa) and the log differential pore volume (ordinate). In FIG. 9 and FIG. 10, Example 1 is indicated by a broken line (thick), Example 2 by a dash-dot line (thin), Example 3 by a broken line (thin), Example 4 by a dotted line, Example 5 by a solid line (thin), Comparative Example 1 by a solid line (thick), and Comparative Example 2 by a dash-dot line (thick).

TABLE 1

| Sample | Surfactant/ monomer (wt %) | Stirring time (min) | Total pore volume (mL/g) | Mean pore radius (μm) | Maximum value of pore radius (μm) | Pore volume* (mL/g) | Pore volume* ratio (%) | Coefficient of variation of pore volume |
|---|---|---|---|---|---|---|---|---|
| Example 1 | 10.6 | 2 | 13.5 | 0.086 | 49.1 | 12.8 | 95.2% | 1.8 |
| Example 2 | 5.0 | 55 | 4.43 | 0.096 | 10.0 | 4.2 | 95.9% | 1.94 |
| Example 3 | 7.5 | 5 | 1.07 | 0.062 | 3.5 | 1.0 | 93.4% | 1.38 |
| Example 4 | 7.5 | 10 | 1.77 | 0.110 | 12.9 | 1.7 | 96.2% | 1.56 |
| Example 5 | 7.5 | 30 | 0.94 | 0.071 | 1.9 | 0.9 | 91.4% | 1.65 |
| Comp. Ex. 1 | — | — | 5.88 | 0.040 | 11.3 | 4.2 | 71.4% | 0.85 |
| Comp. Ex. 2 | — | — | 13 | 0.039 | 100.0 | 11.4 | 87.9% | 1.26 |

*Pore radius of ≥1 μm

The following was confirmed for the samples of Examples 1 to 5.

The ratio of the pore volume of pores with pore radii of 1 μm or greater was at least 90% of the pore volume of all of the pores. The ratio of the pore volume of pores with pore radii of 0.005 μm or smaller was less than 10% of the pore volume of all of the pores. The pore radius at the maximum value of the pore volume was 500 μm or smaller. One of the Examples had a coefficient of variation of the pore distribution of 1.4 or smaller for pores with pore radii of 1 μm or greater (Example 3). Two Examples had a coefficient of variation of the pore distribution of larger than 1.4 for pores with pore radii of 1 μm or greater smaller (Examples 4 and 5). In one Example (Example 5), the region on a side of larger pore radii was broader than the region on a side of smaller pore radii, for the pore radii corresponding to the local maximum value of the pore volume in the pore distribution curve. In one Example (Example 4), the region on a side of smaller pore radii was broader than the region on a side of larger pore radii, for the pore radii corresponding to the local maximum value of the pore volume in the pore distribution curve. Two Examples had at least two local maximum values of the pore volume in the pore distribution curve (Examples 1 and 2). In one Example (Example 2), the two local maximum values of the pore volume in the pore distribution curve were such that the local maximum value of the relatively small pore radii was larger than the local maximum value of the relatively large pore radii. In one Example (Example 1), the two local maximum values of the pore volume in the pore distribution curve were such that the local maximum value of the relatively small pore radii was smaller than the local maximum value of the relatively large pore radii. The total pore volume was 0.9 mL/g or greater. In Comparative Examples 1 and 2, at least the ratio of the pore volume of pores with pore radii of 1 μm or greater was less than 90% of the pore volume of all of the pores.

(b) Relationship Between Bulk Density and Liquid Absorption Rate

Figure 11:
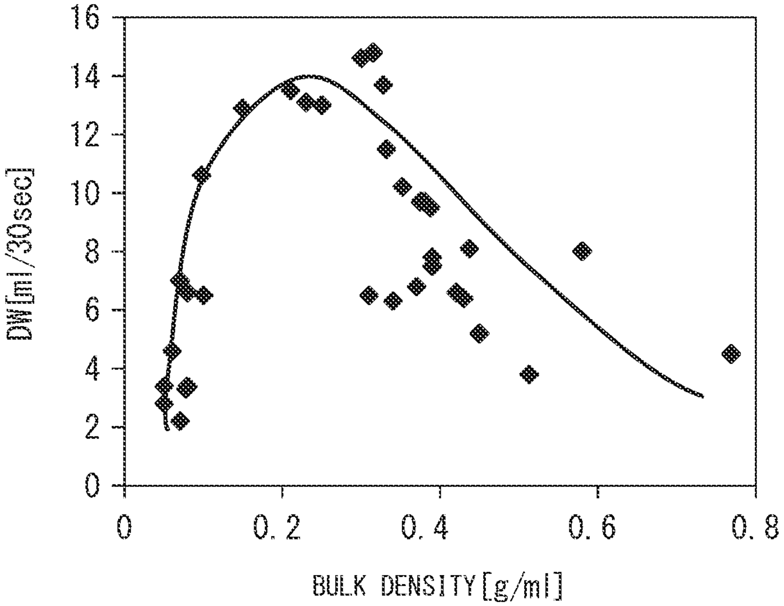
FIG. 11 is a graph showing the relationship between bulk density and absorption performance (DW), for absorbent A.

The measurement results are shown in FIG. 11. FIG. 11 is a graph showing the relationship between the obtained bulk density (abscissa) and the liquid absorption rate (ordinate). As shown in this graph, a bulk density of 0.07 to 0.6 g/cm$^3$ was confirmed to produce a liquid absorption rate (DW) performance of 6 mL/30 sec or greater. It was also confirmed that a bulk density of 0.1 to 0.4 g/cm$^3$ produced a liquid absorption rate (DW) performance of 10 mL/30 sec or greater. It was further confirmed that a bulk density of 0.15 to 0.35 g/cm$^3$ produced a liquid absorption rate (DW) performance of 12 mL/30 sec or greater.

The composite absorbent body of the invention is not particularly restricted and can be applied as a composite absorbent body for a wide range of fields including civil engineering and construction materials such as condensation-proof sheets or simple soil, base materials for pharmaceuticals and the like, and absorption materials for leaking liquids. The liquids to be absorbed by the composite absorbent body are also not particularly restricted, and examples include water and aqueous solutions (such as seawater), acids (such as hydrochloric acid), bases (such as sodium hydroxide), and organic solvents (including alcohols such as methanol and ethanol, ketones such as acetone, ethers such as tetrahydrofuran (THF) and 1,4-dioxane, N,N-dimethylformamide (DMF) and dimethyl sulfoxide (DMSO). Such liquids may also be mixtures of two or more liquids.

The invention is also not restricted to the embodiments described above and can incorporate appropriate combinations, substitutions and modifications within a range that is not outside of the object and gist of the invention. Incidentally, the ordinal terms “first” and “second” as used throughout the present specification serve merely to distinguish between the numbered embodiments and are not used to indicate any relative ordering, precedence or importance.

REFERENCE SIGNS LIST

1 Composite absorbent body

2 First retaining sheet

3 Second retaining sheet
4 Polymer absorbent
5 Superabsorbent polymers (SAP)
6 Hydrophilic fiber sheet

The invention claimed is:

1. A composite absorbent body for absorption of liquid, comprising:

a polymer absorbent comprising a hydrophilic skeleton with communicating pores, wherein a ratio of a pore volume of a pore with a pore radius of 1 μm or greater in the polymer absorbent is 90% or more of a pore volume of the pore, a coefficient of variation of a pore distribution in the pore with the pore radius of 1 μm or greater in the polymer absorbent is larger than 1.4, and the polymer absorbent has at least two local maximum values of the pore volume in a pore distribution curve.

2. The composite absorbent body according to claim 1, wherein the ratio of the pore volume of the pore with the pore radius of 0.005 μm or smaller in the polymer absorbent is less than 10% of the pore volume of the pore.

3. The composite absorbent body according to claim 1, wherein the pore radius at a maximum value of the pore volume in the polymer absorbent is 500 μm or smaller.

4. The composite absorbent body according to claim 1, wherein, for the pore radius corresponding to a local maximum value of the pore volume in a pore distribution curve of the polymer absorbent, a region on a side with a larger pore radius is broader than a region on a side with a smaller pore radius.

5. The composite absorbent body according to claim 1, wherein, for the pore radius corresponding to a local maximum value of the pore volume in a pore distribution curve of the polymer absorbent, a region on a side with a smaller pore radius is broader than a region on a side with a larger pore radius.

6. The composite absorbent body according to claim 1 wherein, of the two local maximum values of the pore volume in the pore distribution curve for the polymer absorbent, a relatively small local maximum value of the pore radius is greater than a relatively large local maximum value of the pore radius.

7. The composite absorbent body according to claim 1 wherein, of the two local maximum values of the pore volume in the pore distribution curve for the polymer absorbent, a relatively small local maximum value of the pore radius is smaller than a relatively large local maximum value of the pore radius.

8. The composite absorbent body according to claim 1, wherein a total pore volume in the polymer absorbent is 0.9 mL/g or greater.

9. The composite absorbent body according to claim 1, wherein a bulk density of the polymer absorbent is 0.07 to 0.6 g/cm$^3$.

10. The composite absorbent body according to claim 1, wherein the polymer absorbent is a monolithic absorbent.

11. The composite absorbent body according to claim 1, wherein the polymer absorbent is a crosslinked polymer hydrolysate of a compound comprising a (meth)acrylic acid ester and two or more vinyl groups in the molecule, and contains at least one or more —COONa group.

12. A polymer absorbent comprising a hydrophilic skeleton with communicating pores, wherein a ratio of a pore volume of a pore with a pore radius of 1 μm or greater is at least 90% of the pore volume of the pore, a coefficient of variation of a pore distribution in the pore with the pore radius of 1 μm or greater in the polymer absorbent is larger than 1.4, and the polymer absorbent has at least two local maximum values of the pore volume in a pore distribution curve.

* * * * *